United States Patent [19]

Kleiner

[11] Patent Number: 5,648,549
[45] Date of Patent: Jul. 15, 1997

[54] PROCESS FOR THE PREPARATION OF SECONDARY ARYLPHOSPHINES

[75] Inventor: Hans-Jerg Kleiner, Kronberg, Germany

[73] Assignee: Hoechst Aktiengesellschaft, Frankfurt, Germany

[21] Appl. No.: 683,532

[22] Filed: Jul. 15, 1996

[30]  Foreign Application Priority Data

Jul. 17, 1995 [DE]  Germany ............. 195 26 047.3

[51] Int. Cl.$^6$ .................................................. C07F 9/50
[52] U.S. Cl. .................................................. 568/17
[58] Field of Search ........................... 568/15, 16, 17

[56]  References Cited

U.S. PATENT DOCUMENTS 2,902,517  9/1959  Schmerling .
3,657,298  4/1972  King et al. .
4,507,503  3/1985  Frey .

FOREIGN PATENT DOCUMENTS 1223838  9/1966  Germany .
1325056  7/1987  U.S.S.R. .

OTHER PUBLICATIONS

*Chemical Abstracts*, vol. 107, No. 23, Bondarenko et al, Dec. 7, 1987, Columbus, Ohio, Abstract No. 217849.
*Chem. Ber.*, vol. 120, Köster et al, Reaktionen des Diphenylphosphanoxids mit Organodiboranen(6) –Sturktur einer zwitterionischen POB–Verbindung, pp. 1117–1123, Dec. 22, 1986.
Studies in Inorganic Chem—20—Phosphorus 1995 D.E.C. Corbridge (Fifth Ed).
Fritzsche, H., et al, *Chem. Ber.* 97, pp. 1988–1993 (1964).
Müller, E., *Houben–Weyl*, "Methoden der organischen Chemie", vol. 12, Stuttgart, Georg Thieme Verlag, 1963, p. 60.

*Primary Examiner*—Gary Geist
*Assistant Examiner*—Jean F. Vollano
*Attorney, Agent, or Firm*—Connolly & Hutz

[57] ABSTRACT

The invention relates to a process for the preparation of secondary phosphines of the formula (I)

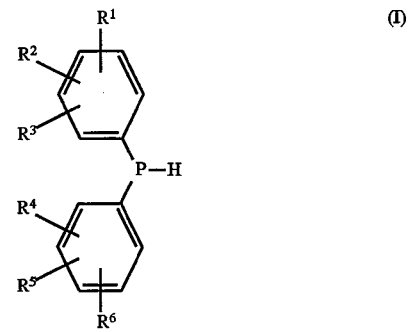

in which $R^1$ to $R^6$ independently of one another are hydrogen, halogen, $(C_1–C_6)$-alkyl or $(C_1–C_6)$-alkoxy, wherein secondary phosphine oxides of the formula (II)

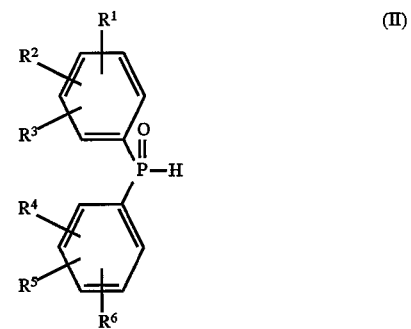

are reacted with Lewis acids as catalysts, at elevated temperature, and the secondary phosphines of the formula (I) formed are distilled off under reduced pressure.

19 Claims, No Drawings

PROCESS FOR THE PREPARATION OF SECONDARY ARYLPHOSPHINES

The invention relates to a process for the preparation of secondary arylphosphines.

Secondary arylphosphines, e.g. diphenylphosphine, are important intermediates for the preparation of phosphorus-containing ligands for numerous catalysts of industrial significance (see e.g. U.S. Pat. No. 3,657,298). They are often prepared by the reduction of suitable trivalent starting compounds, e.g. chlorodiphenylphosphine with lithium aluminum hydride (Houben-Weyl, Methoden der org. Chemie [Methods of Organic Chemistry], volume XII/1, page 60, Georg Thieme Verlag, 1963); there is also often a reduction of pentavalent phosphorus compounds with silanes having an Si—H bond (H. Fritzsche et al., Chem. Ber. 97, 1988 (1964); DE-OS 1223838). These processes are technically expensive and difficult to carry out. In particular, undesirable by-products and having substantial odor nuisance which are obtained have to be taken into account.

The thermal disproportionation of secondary phosphine oxides to the corresponding secondary phosphines and phosphinic acids is also known:

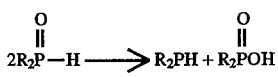

According to SU-PS 1325056 (1987) diphenylphosphine oxide can be split into diphenylphosphine and diphenylphosphinic acid at 165° to 175° C. in the presence of 5 to 10 mol % of diphenylphosphinic acid. However, this process of industrial interest has the disadvantage that the diphenylphosphine prepared contains 15 to 20% of the diphenylphosphine oxide starting material, necessitating a difficult and technically complicated separation of the components.

There was therefore a need for a process which makes it possible to obtain secondary arylphosphines in a technically simple manner and in high yield and purity.

This object is achieved by a process for the preparation of secondary phosphines of the formula (I)

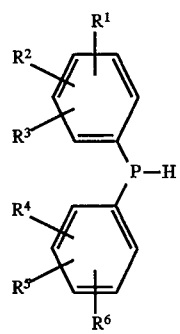

in which $R^1$ to $R^6$ independently of one another are hydrogen, halogen, ($C_1$–$C_6$)-alkyl or ($C_1$–$C_6$)-alkoxy, wherein secondary phosphine oxides of the formula (II)

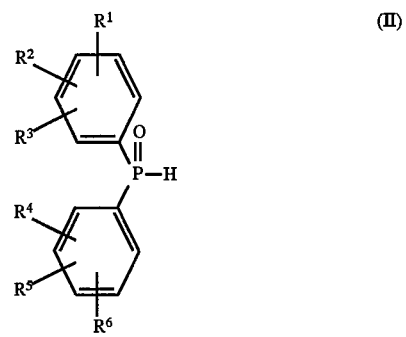

are reacted with Lewis acids as catalysts, at elevated temperature, and the secondary phosphines of the formula (I) formed are distilled off under reduced pressure.

The process is valuable for the preparation of compounds of the formula (I) in which $R^1$ to $R^6$ are hydrogen, fluorine, chlorine, ($C_1$–$C_4$)-alkyl or ($C_1$–$C_4$)-alkoxy.

Important compounds here are those in which 2, especially 3 and preferably 4 of the radicals $R^1$ to $R^6$ are hydrogen.

Examples of alkyl and alkoxy in the radicals $R^1$ to $R^6$ in the compounds (I)/(II) are methyl, ethyl, propyl, isopropyl and the various butyl radicals and, respectively, methoxy and ethoxy.

The process is significant for the preparation of diphenylphosphine, di-p-tolylphosphine, (2-chlorophenyl) phenylphosphine, bis4-fluorophenylphosphine and bis-2-methoxyphenylphosphine.

Suitable Lewis acid catalysts are halides of groups IIb and IIIa of the Periodic Table, good results being obtained with aluminum chloride, zinc chloride and indium chloride. The amount of catalyst is conveniently 0.05 to 2% by weight, preferably 0.1 to 0.5% by weight, based on the compound (II) used.

The starting compounds of the formula (II) are heated together with the catalyst to 140° to 250° C., preferably 150° to 200° C. At the decomposition point of the reaction mixture, which depends on the catalyst, distillation of the secondary phosphines of the formula (I) under reduced pressure begins. When the bulk of the phosphine has been distilled off, the internal temperature is raised further until no more phosphine distills off.

Surprisingly, the phosphines prepared by the process of the present invention are very pure and practically free of the starting materials of the formula (II). Further purification is not normally necessary.

The examples which follow serve to illustrate the invention.

EXAMPLE 1

101 g (0.5 mol) of diphenylphosphine oxide and 0.5 g of aluminum chloride are mixed and heated to 157° C., the pressure being reduced simultaneously (12 mbar). Diphenylphosphine distills off through a descending condenser at a transition temperature of 144° C. The internal temperature is finally raised to 183° C. 42 g of diphenylphosphine are obtained with a purity of 99% according to 31P NMR. That corresponds to a yield of 90% of theory.

EXAMPLE 2

101 g (0.5 mol) of diphenylphosphine oxide and 0.4 g of zinc chloride are mixed and heated to 164° C., the pressure being reduced simultaneously (14 mbar). Diphenylphosphine distills off through a descending condenser at a transition temperature of 148° C. The internal temperature is finally raised to 183° C. 41 g of diphenylphosphine are obtained. That corresponds to a yield of 88% of theory.

EXAMPLE 3

172 g (0.852 mol) of diphenylphosphine oxide and 0.8 g of indium chloride are mixed and heated to 152° C., the pressure being reduced simultaneously (8 mbar). Diphenylphosphine distills off through a descending condenser at a transition temperature of 132° C. After a total of 2 hours, the internal temperature has been raised to 195° C. 70 g of diphenylphosphine are obtained. That corresponds to a yield of 88% of theory.

What is claimed is:

1. A process for the preparation of secondary phosphines of formula (I)

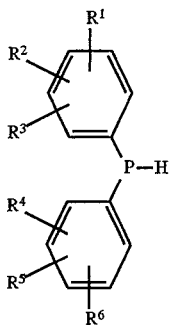

in which $R^1$ to $R^6$ independently of one another are hydrogen, halogen, $(C_1-C_6)$-alkyl or $(C_1-C_6)$-alkoxy, comprising the steps of (a) reacting secondary phosphine oxides of formula (II)

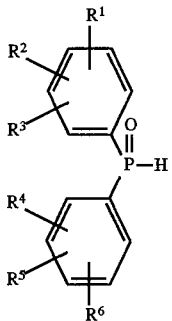

with Lewis acids as catalysts, at elevated temperature, and (b) distilling off, under reduced pressure, secondary phosphines of formula (I) which are formed by the reaction.

2. The process as claimed in claim 1, wherein $R^1$ to $R^6$ independently of one another are hydrogen, fluorine, chlorine, $(C_1-C_4)$-alkyl or $(C_1-C_4)$-alkoxy.

3. The process as claimed in claim 1 wherein at least two of the radicals $R^1$ to $R^6$ are hydrogen.

4. The process as claimed in claim 1 wherein at least three of the radicals $R^1$ to $R^6$ are hydrogen.

5. The process as claimed in claim 1 wherein at least four of the radicals $R^1$ to $R^6$ are hydrogen.

6. The process as claimed in claim 2 wherein at least two of the radicals $R^1$ to $R^6$ are hydrogen.

7. The process as claimed in claim 2 wherein at least three of the radicals $R^1$ to $R^6$ are hydrogen.

8. The process as claimed in claim 2 wherein at least four of the radicals $R^1$ to $R^6$ are hydrogen.

9. The process as claimed in claim 1, wherein formula (I) comprises a secondary phosphine selected from the group consisting of: diphenylphosphine, di-p-tolylphosphine, (2-chlorophenyl)phenylphosphine, bis-4-fluorophenylphosphine and bis-2-methoxyphenylphosphine.

10. The process as claimed in claim 2, wherein formula (I) comprises a secondary phosphine selected from the group consisting of: diphenylphosphine, di-p-tolylphosphine, (2-chlorophenyl)phenylphosphine, bis-4-fluorophenylphosphine and bis-2-methoxyphenylphosphine.

11. The process as claimed in claim 3, wherein formula (I) comprises a secondary phosphine selected from the group consisting of:

diphenylphosphine, di-p-tolylphosphine, (2-chlorophenyl)phenylphosphine, bis-4-fluorophenylphosphine and bis-2-methoxyphenylphosphine.

12. The process as claimed in claim 1, wherein the Lewis acid catalysts used are halides of groups IIb or IIIa of the Periodic Table.

13. The process as claimed in claim 12, wherein the Lewis acid catalysts used are one or more catalysts selected from the group consisting of: aluminum chloride, zinc chloride and indium chloride.

14. The process as claimed in claim 2, wherein the Lewis acid catalysts used are halides of groups IIb or IIIa of the Periodic Table.

15. The process as claimed in claim 14, wherein the Lewis acid catalysts used are one or more catalysts selected from the group consisting of: aluminum chloride, zinc chloride and indium chloride.

16. The process as claimed in claim 1, wherein about 0.05 to about by weight of catalyst is used, based on the compound of formula (II).

17. The process as claimed in claim 1, wherein about 0.1 to about 0.5% by weight of catalyst is used, based on the compound of formula (II).

18. The process as claimed in claim 1, wherein the reaction temperature is about 140° to about 250° C.

19. The process as claimed in claim 1, wherein the reaction temperature is about 150° to about 200° C.

* * * * *